United States Patent
Biyani

(10) Patent No.: US 8,377,013 B2
(45) Date of Patent: Feb. 19, 2013

(54) NEEDLE FOR DIRECTIONAL CONTROL OF THE INJECTION OF BONE CEMENT INTO A VERTEBRAL COMPRESSION FRACTURE

(75) Inventor: Ashok Biyani, Sylvania, OH (US)

(73) Assignee: The University of Toledo, Toledo, OH (US)

( * ) Notice: Subject to any disclaimer, the term of this patent is extended or adjusted under 35 U.S.C. 154(b) by 202 days.

(21) Appl. No.: 12/834,503

(22) Filed: Jul. 12, 2010

(65) Prior Publication Data

US 2011/0034885 A1     Feb. 10, 2011

Related U.S. Application Data

(60) Provisional application No. 61/231,509, filed on Aug. 5, 2009.

(51) Int. Cl.
*A61M 5/32* (2006.01)
*A61B 17/34* (2006.01)
(52) U.S. Cl. ........................ 604/272; 606/185
(58) Field of Classification Search .............. 604/272; 606/185
See application file for complete search history.

(56) References Cited

U.S. PATENT DOCUMENTS

| | | | |
|---|---|---|---|
| 6,132,364 A | 10/2000 | Rottenberg et al. |
| 7,623,902 B2 | 11/2009 | Pacheco |
| 7,670,328 B2 | 3/2010 | Miller |
| 7,699,850 B2 | 4/2010 | Miller |
| 7,722,579 B2 | 5/2010 | Collins et al. |
| 7,722,612 B2 | 5/2010 | Sala et al. |
| 7,789,913 B2 | 9/2010 | Collins et al. |
| 7,811,260 B2 | 10/2010 | Miller et al. |
| 7,811,291 B2 | 10/2010 | Liu et al. |
| 7,815,642 B2 | 10/2010 | Miller |
| 8,034,111 B2 | 10/2011 | Hsu et al. |
| 2004/0024463 A1 | 2/2004 | Thomas, Jr. et al. |
| 2006/0135914 A1 | 6/2006 | Chu et al. |
| 2006/0182780 A1 | 8/2006 | Riley et al. |
| 2006/0195115 A1 | 8/2006 | Ferree |
| 2006/0217736 A1 | 9/2006 | Kaneko et al. |
| 2006/0235338 A1 | 10/2006 | Pacheco |
| 2006/0235417 A1 | 10/2006 | Sala |
| 2006/0264967 A1 | 11/2006 | Ferreyro et al. |
| 2007/0060924 A1 | 3/2007 | Choi |
| 2007/0233249 A1 | 10/2007 | Shadduck |
| 2007/0233250 A1 | 10/2007 | Shadduck |
| 2007/0260258 A1 | 11/2007 | Sommerich |
| 2008/0021312 A1 | 1/2008 | Olson et al. |
| 2008/0021463 A1 | 1/2008 | Georgy |
| 2008/0045857 A1 | 2/2008 | Miller et al. |
| 2008/0045860 A1 | 2/2008 | Miller et al. |
| 2008/0045861 A1 | 2/2008 | Miller et al. |
| 2008/0045965 A1 | 2/2008 | Miller et al. |

(Continued)

*Primary Examiner* — Nicholas Lucchesi
*Assistant Examiner* — Rebecca E Eisenberg
(74) *Attorney, Agent, or Firm* — MacMillan, Sobanski & Todd, LLC

(57) ABSTRACT

A needle for use in a surgical procedure includes an outer cannula including a shaft portion having a side wall and an end wall. A first aperture extends through the side wall of the outer cannula, and a second aperture extending through the end of the outer cannula. The needle also includes an inner cannula that is disposed within the outer cannula and includes a shaft portion having a bore extending therethrough. The inner cannula is selectively movable relative to the outer cannula between a first orientation and a second orientation. In the first orientation, communication is provided between the bore of the inner cannula and a first external region that is located adjacent to the second end of the outer cannula. In the second orientation, communication is provided between the bore of the inner cannula and a second external region that is located adjacent to the second end of the outer cannula.

20 Claims, 4 Drawing Sheets

U.S. PATENT DOCUMENTS

| | | |
|---|---|---|
| 2008/0086143 A1 | 4/2008 | Seaton, Jr. et al. |
| 2008/0195081 A1 | 8/2008 | Moll |
| 2008/0200916 A1 | 8/2008 | Murphy |
| 2008/0300540 A1 | 12/2008 | Lewis |
| 2009/0005790 A1 | 1/2009 | Pacheco |
| 2009/0024025 A1 | 1/2009 | Maschke et al. |
| 2009/0076520 A1 | 3/2009 | Choi |
| 2009/0124895 A1 | 5/2009 | Roden |
| 2009/0131867 A1 | 5/2009 | Liu et al. |
| 2009/0131886 A1 | 5/2009 | Liu et al. |
| 2009/0131945 A1 | 5/2009 | Liu et al. |
| 2009/0131948 A1 | 5/2009 | Liu et al. |
| 2009/0131950 A1 | 5/2009 | Liu et al. |
| 2009/0157085 A1 | 6/2009 | Melsheimer |
| 2009/0163872 A1 | 6/2009 | Tekulve |
| 2009/0198243 A1 | 8/2009 | Melsheimer |
| 2009/0209803 A1 | 8/2009 | Lovoi |
| 2009/0259177 A1 | 10/2009 | Riley et al. |
| 2009/0299282 A1 | 12/2009 | Lau et al. |
| 2009/0299373 A1 | 12/2009 | Sisken |
| 2010/0065989 A1 | 3/2010 | Riley et al. |
| 2010/0069786 A1* | 3/2010 | Globerman et al. .......... 600/564 |
| 2010/0100132 A1 | 4/2010 | Pacheco |
| 2010/0215213 A1 | 8/2010 | Mielekamp et al. |
| 2010/0228358 A1 | 9/2010 | Leonard et al. |
| 2010/0286616 A1* | 11/2010 | Baroud .................... 604/164.11 |

\* cited by examiner

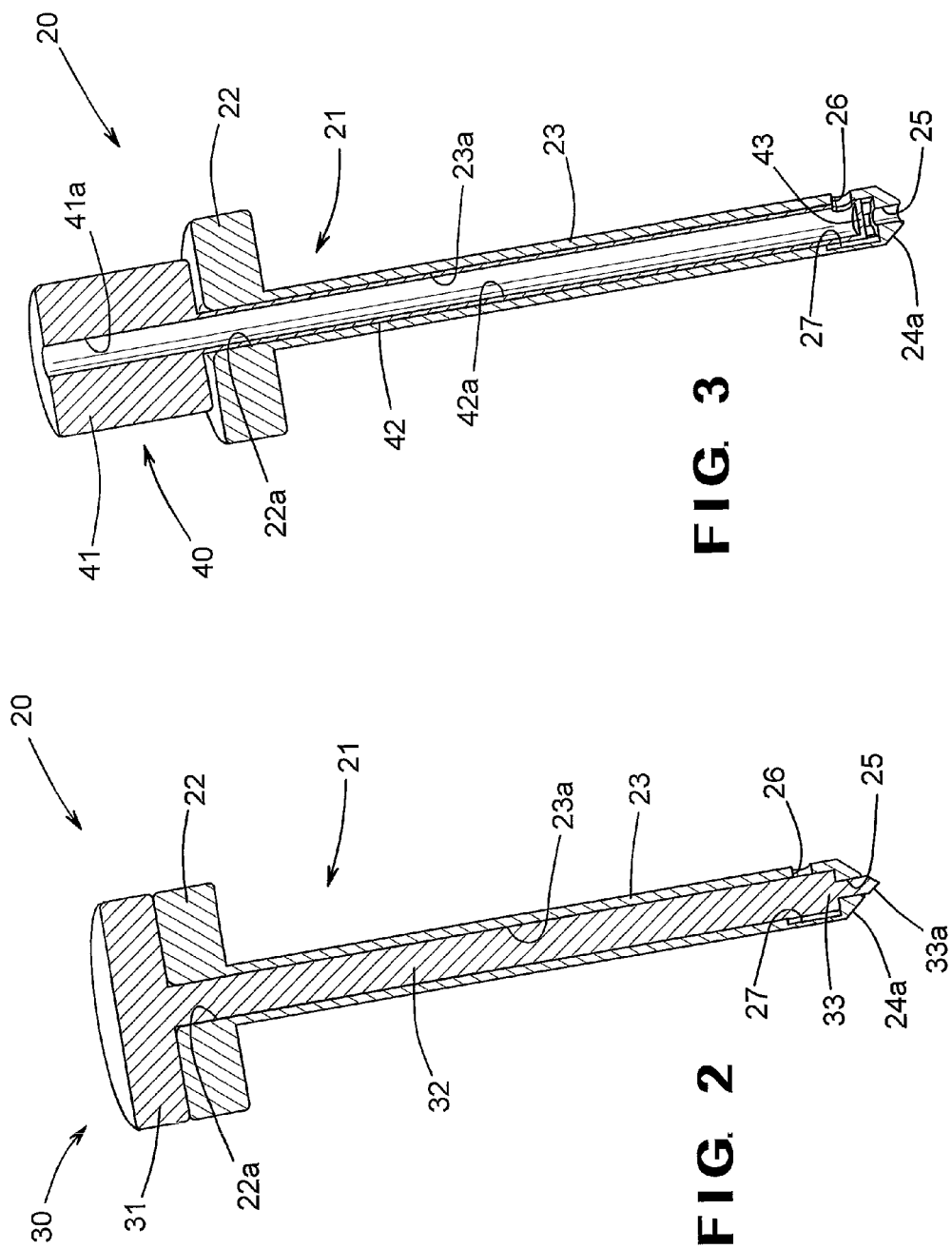

NEEDLE FOR DIRECTIONAL CONTROL OF THE INJECTION OF BONE CEMENT INTO A VERTEBRAL COMPRESSION FRACTURE

STATEMENTS REGARDING FEDERALLY SPONSORED RESEARCH OR DEVELOPMENT AND CROSS-REFERENCE TO RELATED APPLICATIONS

This invention was not made with any government support. This application claims the benefit of U.S. Provisional Application No. 61/231,509, filed Aug. 5, 2009, the disclosure of which is incorporated herein by reference.

BACKGROUND OF THE INVENTION

This invention relates in general to the field of orthopedic surgery including, more specifically, the field of spinal surgery. In particular, this invention relates to an improved structure for a needle that can provide selective directional control of the injection of a bone cement or other material into a fractured bone, such as a vertebra of a spine, during a spinal surgical procedure.

A compression fracture is a common fracture of a vertebra of the spine. In a typical compression fracture, the vertebra has suffered a crush or wedging injury. Vertebral compression fractures are common, especially in older adults who suffer from osteoporosis. Traditional conservative treatment includes bed rest, pain control, and physical therapy. For those patients who do not respond to conservative treatment, interventional procedures such as kyphoplasty and vertebroplasty can be considered. During a kyphoplasty procedure, a void is created within the fractured vertebra by initially inflating a balloon therein, then injecting a bone cement material under a relatively low pressure into the void. During a vertebroplasty procedure, a relatively high viscosity bone cement material is injected directly into the fractured vertebra without the initial creation of a void by balloon inflation.

In both of these procedures, the bone cement material may be injected into the fractured vertebra using a vertebral needle that can facilitate the directional flow of bone cement material to a desired location, thus improving the fill of the bone cement material within the vertebra. Most currently available vertebral needles allow the bone cement material to be injected either only (1) axially straight through a hole provided at the tip of the vertebral needle or (2) radially sideways through a hole provided in the sidewall of the vertebral needle. Thus, to optimize the control of the flow of the bone cement material into the vertebra, both of the two known types of the vertebral needles need to be used during the course of the surgical procedure. However, the intra-operative changing of the vertebral needles is relatively difficult and time consuming. Thus, it would be desirable to provide an improved structure for a needle that can provide selective directional control of the injection of a bone cement or other material into a fractured bone, such as a vertebra of a spine, during such a spinal surgical procedure.

SUMMARY OF THE INVENTION

This invention relates to an improved structure for a needle that can provide selective directional control of the injection of a bone cement or other material into a fractured bone, such as a vertebra of a spine, during a spinal surgical procedure. The needle includes an outer cannula including a shaft portion having a side wall and an end wall. A first aperture extends through the side wall of the outer cannula, and a second aperture extending through the end of the outer cannula. The needle also includes an inner cannula that is disposed within the outer cannula and includes a shaft portion having a bore extending therethrough. The inner cannula is selectively movable relative to the outer cannula between a first orientation and a second orientation. In the first orientation, communication is provided between the bore of the inner cannula and a first external region that is located adjacent to the second end of the outer cannula. In the second orientation, communication is provided between the bore of the inner cannula and a second external region that is located adjacent to the second end of the outer cannula.

Various aspects of this invention will become apparent to those skilled in the art from the following detailed description of the preferred embodiment, when read in light of the accompanying drawings.

BRIEF DESCRIPTION OF THE DRAWINGS

FIG. 2 is a sectional perspective view of the vertebral needle illustrated in FIG. 1 showing an outer cannula having a solid obturator disposed therein.

FIG. 3 is a sectional perspective view similar to FIG. 2 showing the outer cannula having an inner cannula disposed therein in place of the solid obturator.

DETAILED DESCRIPTION OF THE PREFERRED EMBODIMENT

Figure 1:
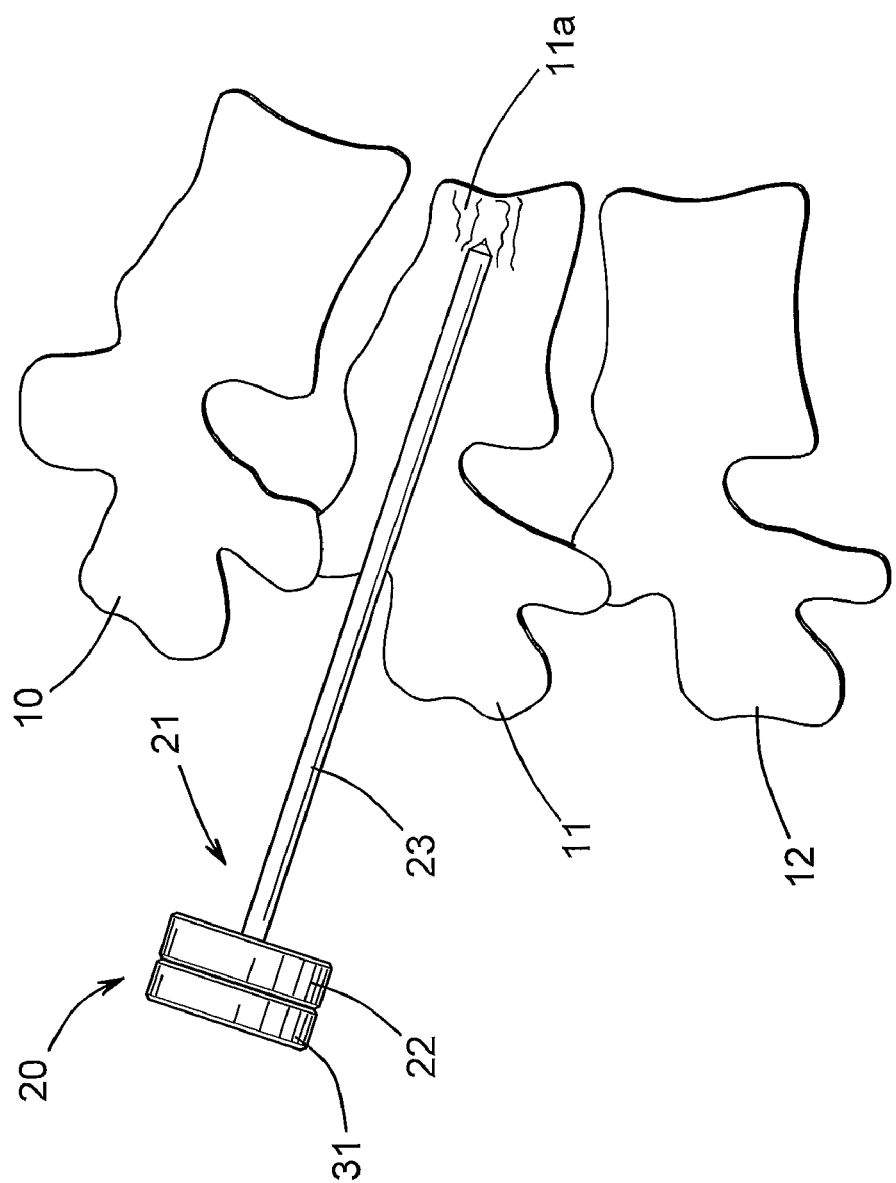
FIG. 1 is schematic side elevational view of three vertebrae of a portion of a human spine, wherein the upper and lower vertebrae are undamaged and the intermediate vertebra has experienced a compression fracture, and wherein a vertebral needle in accordance with this invention is shown inserted into the damaged vertebra.
Figure 4:
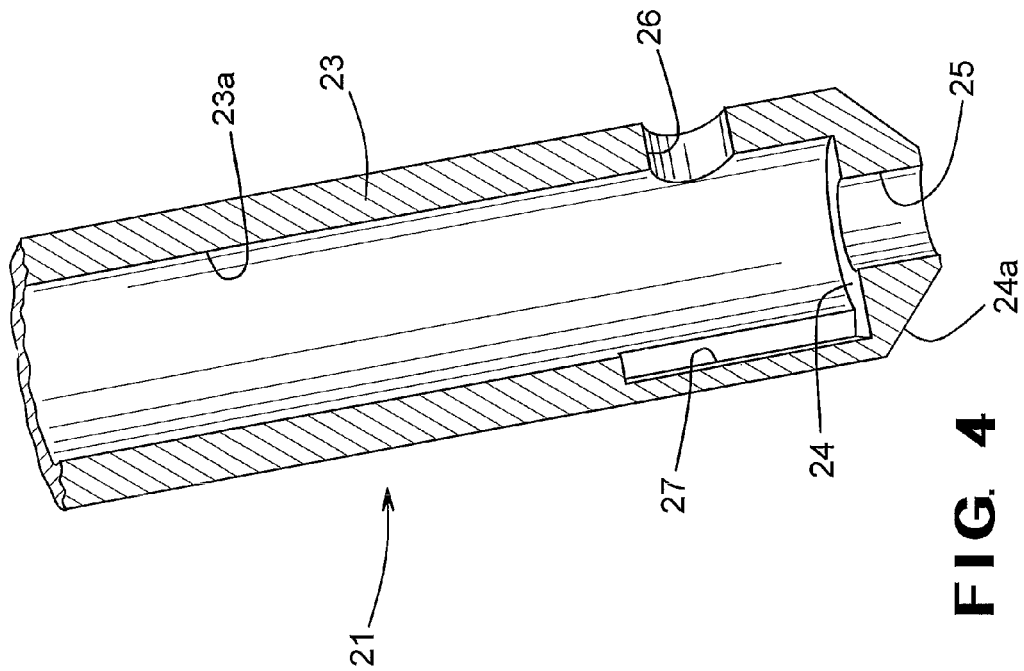
FIG. 4 is an enlarged sectional perspective view of an end of the outer cannula illustrated in FIGS. 1, 2, and 3.
Figure 5:
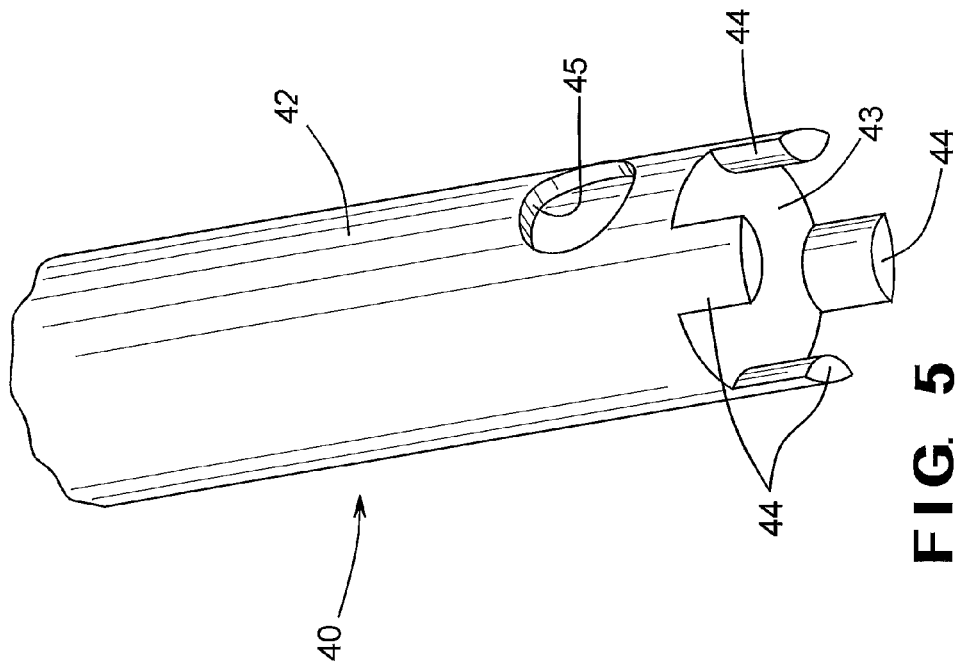
FIG. 5 is an enlarged sectional perspective view of an end of the inner cannula illustrated in FIG. 3.

Referring now to the drawings, there is illustrated in FIG. 1 three vertebrae 10, 11, and 12 of a portion of a human spine. The three vertebrae 10, 11, and 12 may be located in any region of the human spine, but typically are located in the thoracic and lumbar regions. In the illustrated embodiment, the upper vertebra 10 and the lower vertebra 12 are undamaged, while the intermediate vertebra 11 has experienced a compression fracture as shown at 11a. As a result of such compression fracture 11a, the intermediate vertebra 11 can become collapsed between the upper vertebra 10 and the lower vertebra 12, which can cause pain or an abnormal curvature of the spine. Although this invention will be described and illustrated in the context of repairing the compression fracture 11a of the intermediate vertebra 11, it will be appreciated that this invention may be practiced in connection with any other desired surgical procedure and for any other desired purpose.

A vertebral needle, indicated generally at 20, is provided to treat the vertebral compression fracture 11a of the intermediate vertebra 11. As shown in FIG. 1, the vertebral needle 20 can be inserted into the intermediate vertebra 11 such that an end thereof is disposed within or adjacent to the region of the compression fracture 11a. As will be explained in detail below, the vertebral needle 20 is adapted to facilitate the injection of a convention bone cement or other material into the region of the compression fracture 11a during an interventional procedure, such as kyphoplasty and vertebroplasty, to quickly and effectively ameliorate the condition.

The structure of the vertebral needle 20 is illustrated in FIGS. 2 through 7. As best shown in FIG. 2, the vertebral needle 20 includes an outer cannula, indicated generally at 21, having a head portion 22 and a shaft portion 23. The illustrated head portion 22 is generally hollow and cylindrical in shape and has an axially extending bore 22a provided therein that defines an inner surface. However, the head portion 22 of the outer cannula 21 can have any desired shape. The illustrated shaft portion 23 is also generally hollow and cylindrical in shape and has an axially extending bore 23a provided through a side wall therein having an inner surface that defines an interior space. However, the shaft portion 23 of the outer cannula 21 can have any desired shape. The inner surfaces of the bores 22a and 23a of the head portion 22 and the shaft portion 23, respectively, are preferably axially aligned, although such is not required. In the illustrated embodiment, the head portion 22 and the shaft portion 23 of the outer cannula 21 are formed from a single piece of material, although such is not required. The head portion 22 and the shaft portion 23 may be formed from any desired material or combination of materials, such as titanium, stainless steel, cobalt-chrome, or any other suitable biomaterial.

The head portion 22 of the outer cannula 21 is provided at a first end of the shaft portion 23 thereof. A second opposite end of the shaft portion 23 terminates in an end wall 24 that closes the bore 23a formed therethrough. In the illustrated embodiment, the end wall 24 has an outer surface 24a that is tapered toward a point. However, the end wall 24 of the outer cannula 21 may have any desired shape. First and second apertures 25 and 26 are provided in the second end of the shaft portion 23. The first aperture 25 extends axially through the end wall 24 and provides communication between the bore 23a and an external region that is located axially adjacent to the second end of the outer cannula 21. The second aperture 26 extends radially through the side wall of the shaft portion 23 and provides communication between the bore 23a and an external region that is located radially adjacent to the second end of the outer cannula 21. Additionally, a recessed area 27 is provided on the inner surface of the bore 23a adjacent to the first aperture 25. The purposes for the first aperture 25, the second aperture 26, and the recessed area 27 will be explained below.

As shown in FIG. 2, the vertebral needle 20 also includes an obturator, indicated generally at 30, having a head portion 31 and a shaft portion 32. The illustrated head portion 31 is generally cylindrical in shape. However, the head portion 31 of the obturator 30 can have any desired shape. The illustrated shaft portion 32 is also generally cylindrical in shape and defines an outer surface. However, the shaft portion 32 of the obturator 30 can have any desired shape. The obturator 30 is supported on the outer cannula 21 for movement relative thereto. In the illustrated embodiment, the outer surface of the shaft portion 32 of the obturator 30 is supported for sliding movement on the inner surface of the bore 23a of the shaft portion 23 of the outer cannula 21. The obturator 30 has a tip portion 33 that, in the illustrated embodiment, includes a tapered end surface 33a. In the illustrated embodiment, the head portion 31 and the shaft portion 32 of the obturator 30 are formed from a single piece of material, although such is not required. The head portion 31 and the shaft portion 32 may be formed from any desired material or combination of materials, such as titanium, stainless steel, cobalt-chrome, or any other suitable biomaterial.

The obturator 30 can be located in an installation position (illustrated in FIG. 2) relative to the outer cannula 21. In this installation position, the head portion 31 of the obturator 30 abuts the head portion 22 of the outer cannula 21. In this manner, the obturator 30 can be positively positioned relative to the outer cannula 21. When the obturator 30 is located in the installation position, the tip portion 33 of the obturator 30 extends through the first aperture 25 provided through the end wall 24 of the outer cannula 21. Thus, the tip portion 33 blocks the first aperture 25, thereby preventing communication between the bore 23a and the external region that is located axially adjacent to the second end of the outer cannula 21. Preferably, the tapered end surface 33a of the tip portion 33 of the obturator 30 is generally co-extensive with the outer surface 24a of the end wall 24 of the outer cannula 21 such that the outer cannula 21 and the obturator 30 cooperate to present a pointed tip at the second end of the vertebral needle 20. The purpose for this pointed tip will be explained below. Additionally, when the obturator 30 is located in the installation position shown in FIG. 2, the tip portion 33 blocks the second aperture 26, thereby preventing communication between the bore 23a and the external region that is located radially adjacent to the second end of the outer cannula 21. The purpose for such blockage will be explained below.

Figure 6:
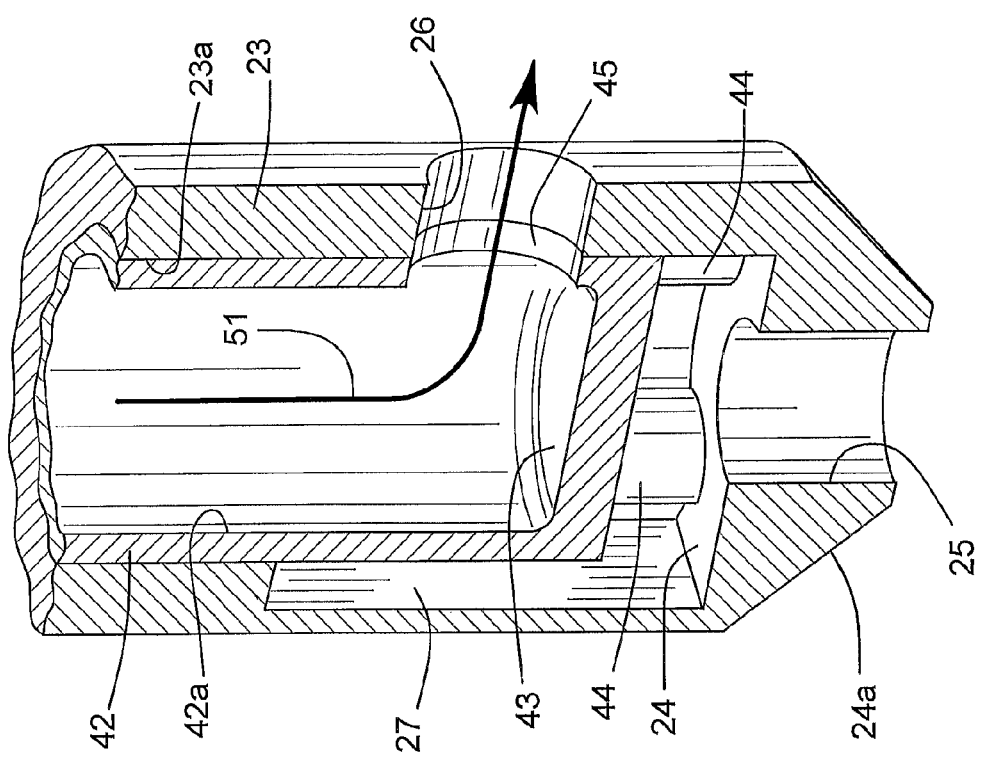
FIG. 6 is an enlarged sectional perspective view of an end of the assembled vertebral needle illustrated in FIG. 3, wherein the inner cannula is positioned in a first orientation relative to the outer cannula.
Figure 7:
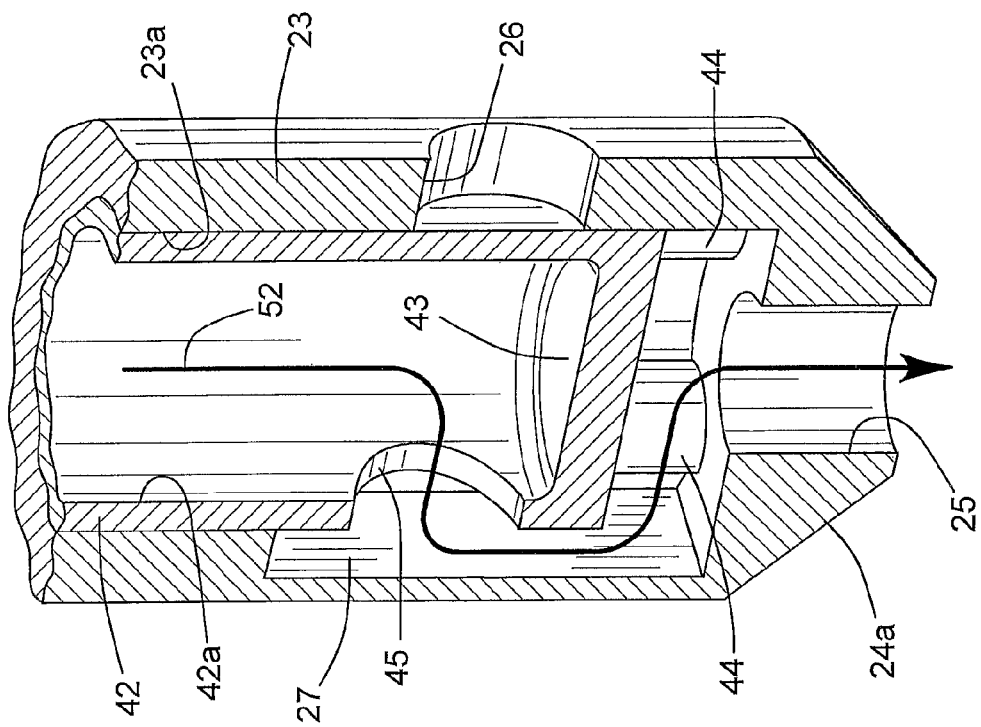
FIG. 7 is an enlarged sectional perspective view of the end of the assembled vertebral needle illustrated in FIG. 6, wherein the inner cannula is positioned in a second orientation relative to the outer cannula.

As shown in FIGS. 3, 6, and 7, the obturator 30 can be removed from the outer cannula 21, and an inner cannula, indicated generally at 40, and be disposed in its stead. The inner cannula 40 includes a head portion 41 and a shaft portion 42. The illustrated head portion 41 is generally hollow and cylindrical in shape and has an axially extending bore 41a provided therein that defines an inner surface. However, the head portion 41 of the inner cannula 40 can have any desired shape. The illustrated shaft portion 42 is also generally hollow and cylindrical in shape and has an axially extending bore 42a provided therein having an inner surface that defines an interior space. However, the shaft portion 42 of the inner cannula 40 can have any desired shape. The inner surfaces of the bores 41a and 42a of the head portion 41 and the shaft portion 42, respectively, are preferably axially aligned, although such is not required. In the illustrated embodiment, the head portion 41 and the shaft portion 42 of the inner cannula 40 are formed from a single piece of material, although such is not required. The head portion 41 and the shaft portion 42 may be formed from any desired material or combination of materials, such as titanium, stainless steel, cobalt-chrome, or any other suitable biomaterial.

The head portion 41 of the inner cannula 40 is provided at a first end of the shaft portion 42 thereof. A second opposite end of the shaft portion 42 terminates in an end wall 43 that closes the bore 42a formed therethrough. One or more spacers 44 may be provided on the outer surface of the end wall 43. In the illustrated embodiment, four equally sized and shaped spacers 44 extend axially from the end wall 43 of the inner cannula 40. However, the spacers 44 may be provided having any desired shape or combination of shapes. An aperture 45 is provided through a side wall in the second end of the shaft portion 42 of the inner cannula 40. The aperture 45 extends radially through the side wall of the shaft portion 42 and provides communication between the bore 42a and an external region that is located radially adjacent to the second end of the inner cannula 40. The spacers 44 engage the end wall 24 of the outer cannula 21 so as to maintain a space between the end wall 43 of the inner cannula 40 and the end wall 24 of the outer cannula 21.

As best shown in FIGS. 6, and 7, the inner cannula 40 can be selectively positioned in first and second orientations relative to the outer cannula 21. FIG. 6 shows the inner cannula 40 positioned in the first orientation relative to the outer cannula 21. In this first orientation, the aperture 45 that extends radially through the side wall of the shaft portion 42 of the inner cannula 40 is aligned with the second aperture 26 that extends radially through the side wall of the shaft portion 23 of the outer cannula 21. This alignment of the apertures 45 and 26 provides communication between the bore 42a provided within the shaft portion 42 of the inner cannula 40 and the external region that is located radially adjacent to the second end of the outer cannula 21, as shown by the arrow 51 in FIG. 6. At same time, the end wall 43 of the inner cannula 40 prevents communication between the bore 42a provided within the shaft portion 42 of the inner cannula 40 and the external region that is located axially adjacent to the second end of the outer cannula 21.

FIG. 7 shows the inner cannula 40 positioned in the second orientation relative to the outer cannula 21. In this second orientation, the aperture 45 that extends radially through the side wall of the shaft portion 42 of the inner cannula 40 is aligned with the recessed area 27 that is provided in the side wall of the shaft portion 23 of the outer cannula 21. This alignment of the aperture 45 and the recessed area 27 provides communication between the bore 42a provided within the shaft portion 42 of the inner cannula 40 and the external region that is located axially adjacent to the second end of the outer cannula 21, as shown by the arrow 52 in FIG. 7. At same time, the side wall of the shaft portion 42 of the inner cannula 40 prevents communication between the bore 42a provided within the shaft portion 42 of the inner cannula 40 and the external region that is located radially adjacent to the second end of the outer cannula 21.

The inner cannula 40 can be selectively positioned in first and second orientations relative to the outer cannula 21 quickly and easily by rotating the inner cannula 40 relative to the outer cannula 21. If desired, one or more indicia (not shown) may be provided on either or both of the inner cannula 40 and the outer cannula 21 to provide a visual indication of when the first and second orientations have been achieved. Alternatively, one or more conventional detents, stops, or other structures (not shown) may be provided on either or both of the inner cannula 40 and the outer cannula 21 to provide a tactile indication of when the first and second orientations have been achieved.

The method of operation of the vertebral needle 20 will now be explained. Initially, the obturator 30 is installed within the outer cannula 21 and positioned in the installation position illustrated in FIG. 2. As mentioned above, when the obturator 30 is located in the installation position, the tip portion 33 of the obturator 30 extends through the first aperture 25 provided through the end wall 24 of the outer cannula 21. Additionally, the tip portion 33 of the obturator 30 blocks the second aperture 26 provided through the side wall of the shaft portion 23 of the outer cannula 21, thereby preventing communication between the bore 23a and the external region that is located radially adjacent to the second end of the outer cannula 21. The assembly of the outer cannula 21 and the obturator 30 can then be inserted through a relatively small incision until the tip portion 33 of the obturator 30 engages a desired location on the surface of the intermediate vertebra 11.

As mentioned above, the tapered end surface 33a of the tip portion 33 of the obturator 30 is preferably co-extensive with the outer surface 24a of the end wall 24 of the outer cannula 21 such that the outer cannula 21 and the obturator 30 cooperate to present a pointed tip at the second end of the vertebral needle 20. This pointed tip is adapted for impaction into the desired location by utilizing a conventional tool, such as an orthopedic mallet. The precise location where the tip portion 33 of the obturator 30 engages the surface of the intermediate vertebra 11 is usually determined using conventional fluoroscopic or other imaging or navigational techniques. The assembly of the outer cannula 21 and the obturator 30 is continued to be inserted until the tip portion 33 of the obturator 30 is disposed within the compression fracture 11a within the intermediate vertebra 11.

Next, the obturator 30 is removed from the outer cannula 21, and the inner cannula 40 is inserted within the outer cannula 21, as shown in FIG. 3. As discussed above, the inner cannula 40 can be selectively positioned in either of the first and second orientations relative to the outer cannula 21. Such relative positioning provides selective directional control of the injection of a bone cement or other material into the compression fracture 11a within the intermediate vertebra 11. To accomplish this, a quantity of the bone cement or other material is initially inserted within the vertebral needle 20 through the bore 41a provided in the head portion 41 of the inner cannula 40. Such bone cement or other material can then moved through the shaft portion 42 of the inner cannula 40 in any conventional manner, such as under pressure or by means of a conventional plunger (not shown). A preferred method would include a threaded or otherwise secure locking mechanism that would allow attachment of a cement containing device (not shown) to the delivery cannula. The cement containing device may come in the form of currently available threaded syringe or other similar mechanisms that facilitate controlled extrusion of the cement material.

When the inner cannula 40 positioned in the first orientation relative to the outer cannula 21 shown in FIG. 6, the bone cement or other material will follow the path indicated by the arrow 51 into the external region that is located radially adjacent to the second end of the outer cannula 21. When the inner cannula 40 positioned in the second orientation relative to the outer cannula 21 shown in FIG. 7, the bone cement or other material will follow the path indicated by the arrow 52 into the external region that is located radially adjacent to the second end of the outer cannula 21. Thus, the vertebral needle provides selective directional control of the injection of the bone cement or other material quickly and easily.

In the illustrated embodiment, the outer cannula 21 and the inner cannula 40 are structured in such a manner that the bone cement or other material pass outwardly from either, but not both, of the first and second apertures 25 and 26. However, it will be appreciated that the outer cannula 21 and the inner cannula 40 could be structured to provide an intermediate relative orientation wherein the bone cement or other material could pass outwardly from both of the first and second apertures 25 and 26 simultaneously. Also, it will be appreciated that either or both of the outer cannula 21 and the inner cannula 40 can be provided with a greater number of apertures to provide additional selective relative positioning for greater directional control of the injection of the bone cement or other material.

The principle and mode of operation of this invention have been explained and illustrated in its preferred embodiment. However, it must be understood that this invention may be practiced otherwise than as specifically explained and illustrated without departing from its spirit or scope.

What is claimed is:

1. A needle for use in a surgical procedure comprising:
an outer cannula including a hollow shaft portion defining an interior space and having a first wall and a second wall, wherein a first aperture extends through the first wall of the outer cannula and a second aperture extends through the second wall of the outer cannula; and
an inner cannula disposed within the interior space of the shaft portion of the outer cannula, the inner cannula including a hollow shaft portion defining an interior space, the inner cannula being selectively movable relative to the outer cannula between a first orientation, wherein communication is provided from the interior space of the inner cannula to the first aperture provided in the outer cannula, and a second orientation, wherein communication is provided from the interior space of the inner cannula to the second aperture provided in the outer cannula,
wherein the hollow shaft portion of the inner cannula has an aperture provided therein that provides communication from the interior space of the inner cannula to the first aperture provided in the outer cannula when the inner cannula is in the first orientation and provides communication from the interior space of the inner cannula to the second aperture provided in the outer cannula when the inner cannula is in the second orientation.

2. The needle defined in claim 1 wherein the outer cannula is generally cylindrical in shape, and wherein the first wall of the outer cannula is an axial end wall thereof and the second wall of the outer cannula is a radial side wall thereof.

3. The needle defined in claim 1 wherein the hollow shaft portion of the outer cannula includes an inner surface having a recess provided therein, and wherein communication is provided from the interior space of the inner cannula through the recess to the first aperture provided in the outer cannula when the inner cannula is in the first orientation.

4. The needle defined in claim 1 wherein the inner cannula is rotatably movable relative to the outer cannula between the first orientation and the second orientation.

5. The needle defined in claim 1 wherein the inner cannula includes a head portion that extends from the hollow shaft portion.

6. The needle defined in claim 5 wherein the head portion of the inner cannula is hollow and includes an interior space that communicates with the interior space of the hollow shaft portion of the inner cannula.

7. The needle defined in claim 1 further including an obturator that can be disposed within the outer cannula in lieu of the inner cannula.

8. The needle defined in claim 7 wherein the obturator blocks the first aperture provided in the outer cannula when disposed in the outer cannula.

9. The needle defined in claim 7 wherein the obturator blocks the second aperture provided in the outer cannula when disposed in the outer cannula.

10. The needle defined in claim 7 wherein the obturator blocks both the first aperture and the second aperture provided in the outer cannula when disposed in the outer cannula.

11. The needle defined in claim 7 wherein the obturator has a pointed tip that extends through the first aperture provided in the outer cannula when disposed in the outer cannula.

12. A needle for use in a surgical procedure comprising:
an outer cannula including a hollow shaft portion defining an interior space and having a first wall and a second wall, wherein a first aperture extends through the first wall of the outer cannula and a second aperture extends through the second wall of the outer cannula; and
an inner cannula disposed within the interior space of the shaft portion of the outer cannula, the inner cannula including a hollow shaft portion defining an interior space, the inner cannula being selectively movable relative to the outer cannula between a first orientation, wherein communication is provided from the interior space of the inner cannula to the first aperture provided in the outer cannula, and a second orientation, wherein communication is provided from the interior space of the inner cannula to the second aperture provided in the outer cannula,
wherein the hollow shaft portion of the inner cannula has an aperture provided therein, and wherein the hollow shaft portion of the outer cannula includes an inner surface having a recess provided therein, wherein communication is provided from the interior space of the inner cannula through the inner cannula aperture and the recess to the first aperture provided in the outer cannula when the inner cannula is in the first orientation.

13. A needle for use in a surgical procedure comprising:
an outer cannula including a hollow shaft portion defining an interior space and having a first wall and a second wall, wherein a first aperture extends through the first wall of the outer cannula and a second aperture extends through the second wall of the outer cannula; and
an inner cannula disposed within the interior space of the shaft portion of the outer cannula, the inner cannula including a hollow shaft portion defining an interior space, the inner cannula being selectively movable relative to the outer cannula between a first orientation, wherein communication is provided from the interior space of the inner cannula to the first aperture provided in the outer cannula, and a second orientation, wherein communication is provided from the interior space of the inner cannula to the second aperture provided in the outer cannula,
wherein the inner cannula includes a wall having a spacer extending therefrom that engages the first wall of the outer cannula so as to maintain a space between the wall of the inner cannula and the first wall of the outer cannula.

14. The needle defined in claim 13 wherein the inner cannula includes a wall having a plurality of spacers extending therefrom that engages the first wall of the outer cannula so as to maintain a space between the wall of the inner cannula and the first wall of the outer cannula.

15. A needle for use in a surgical procedure comprising:
an outer cannula including a hollow shaft portion defining an interior space and having a first wall and a second wall, wherein a first aperture extends through the first wall of the outer cannula and a second aperture extends through the second wall of the outer cannula; and
an inner cannula disposed within the interior space of the shaft portion of the outer cannula, the inner cannula including a hollow shaft portion defining an interior space, the inner cannula being selectively movable relative to the outer cannula between a first orientation, wherein communication is provided from the interior space of the inner cannula to the first aperture provided in the outer cannula, and a second orientation, wherein communication is provided from the interior space of the inner cannula to the second aperture provided in the outer cannula,
wherein the inner cannula is generally cylindrical in shape and includes an axial end wall having a spacer extending therefrom that engages the first wall of the outer cannula so as to maintain a space between the axial end wall of the inner cannula and the first wall of the outer cannula.

16. A needle for use in the injection of a bone cement or other material into a fractured bone during a surgical procedure comprising:
   an outer cannula including a hollow shaft portion defining an interior space and having a first wall and a second wall, wherein a first aperture extends through the first wall of the outer cannula and a second aperture extends through the second wall of the outer cannula;
   an inner cannula disposed within the interior space of the shaft portion of the outer cannula, the inner cannula including a hollow shaft portion defining an interior space, the inner cannula being selectively movable relative to the outer cannula between a first orientation, wherein communication is provided from the interior space of the inner cannula to the first aperture provided in the outer cannula, and a second orientation, wherein communication is provided from the interior space of the inner cannula to the second aperture provided in the outer cannula; and
   a plunger disposed within the inner cannula and adapted to cause a bone cement or other material to be injected through the needle into a fractured bone during a surgical procedure.

17. The needle defined in claim 16 wherein the hollow shaft portion of the outer cannula includes an inner surface having a recess provided therein, and wherein communication is provided from the interior space of the inner cannula through the recess to the first aperture provided in the outer cannula when the inner cannula is in the first orientation.

18. The needle defined in claim 16 wherein the inner cannula is rotatably movable relative to the outer cannula between the first orientation and the second orientation.

19. The needle defined in claim 16 wherein the inner cannula includes a wall having a spacer extending therefrom that engages the first wall of the outer cannula so as to maintain a space between the wall of the inner cannula and the first wall of the outer cannula.

20. The needle defined in claim 16 further including an obturator that can be disposed within the outer cannula in lieu of the inner cannula.

* * * * *